(12) United States Patent
SenGupta et al.

(10) Patent No.: US 7,378,466 B2
(45) Date of Patent: May 27, 2008

(54) NONVISCOUS AQUEOUS DISPERSION COMPOSITIONS OF WATER-SWELLABLE LAYERED SILICATES AND THE METHOD OF PRODUCING THE SAME

(75) Inventors: Ashoke K. SenGupta, Barrington, IL (US); Jerald W. Darlington, Jr., Marengo, IL (US); Jennifer Gould, Sheboygan, WI (US); Iiona Lin, Arlington Heights, IL (US)

(73) Assignee: AMCOL International Corp., Arlington Heights, IL (US)

( * ) Notice: Subject to any disclaimer, the term of this patent is extended or adjusted under 35 U.S.C. 154(b) by 216 days.

(21) Appl. No.: 10/706,752

(22) Filed: Nov. 12, 2003

(65) Prior Publication Data

US 2004/0229991 A1    Nov. 18, 2004

Related U.S. Application Data

(60) Provisional application No. 60/425,862, filed on Nov. 13, 2002.

(51) Int. Cl.
*A61K 8/26* (2006.01)
*A61K 7/06* (2006.01)

(52) U.S. Cl. .......... 524/445; 524/447; 501/145; 424/401; 424/70.1

(58) Field of Classification Search .......... 132/202; 524/445, 186
See application file for complete search history.

(56) References Cited

U.S. PATENT DOCUMENTS

| | | | | |
|---|---|---|---|---|
| 3,711,573 A | * | 1/1973 | Nagy | 525/531 |
| 4,390,033 A | | 6/1983 | Khalil et al. | |
| 4,761,249 A | * | 8/1988 | Giede et al. | 8/137 |
| 5,089,252 A | * | 2/1992 | Grollier et al. | 424/47 |
| 5,112,603 A | * | 5/1992 | Nadolsky et al. | 514/772.3 |
| 5,171,565 A | * | 12/1992 | Akhtar et al. | 424/70.4 |
| 5,556,547 A | * | 9/1996 | Kajita | 210/749 |
| 5,575,924 A | * | 11/1996 | Bair et al. | 210/734 |
| 5,670,435 A | * | 9/1997 | Kajita | 502/81 |
| 5,721,306 A | * | 2/1998 | Tsipursky et al. | 524/449 |
| 5,843,875 A | * | 12/1998 | Wei et al. | 510/101 |
| 6,399,690 B2 | * | 6/2002 | Lan et al. | 524/445 |
| 6,500,411 B2 | * | 12/2002 | SenGupta et al. | 424/59 |
| 6,544,500 B1 | * | 4/2003 | O'Toole et al. | 424/70.1 |
| 6,712,934 B2 | * | 3/2004 | Ahlgren et al. | 162/181.6 |
| 6,939,536 B2 | * | 9/2005 | Chen et al. | 424/70.1 |
| 2002/0182155 A1 | | 12/2002 | SenGupta et al. | |
| 2003/0108501 A1 | * | 6/2003 | Hofrichter et al. | 424/70.1 |
| 2003/0163877 A1 | * | 9/2003 | Baker et al. | 8/405 |
| 2004/0103483 A1 | * | 6/2004 | Delplancke et al. | 8/115.51 |
| 2005/0112074 A1 | * | 5/2005 | Arai et al. | 424/70.1 |

FOREIGN PATENT DOCUMENTS

| | | | |
|---|---|---|---|
| EP | 0559319 | | 9/1993 |
| GB | 2364047 | | 1/2002 |
| WO | WO 99/25312 | * | 5/1999 |
| WO | WO-0200557 | | 1/2002 |

OTHER PUBLICATIONS

Hawley's Condensed Chemical Dictionary. Fourteenth Edition. Lewis, Richard. Electronic Version, 2002. "bentonite" and "hectorite".*
PCT International Search Report dated Mar. 31, 2004 for International Application No. PCT/US03/36040.

* cited by examiner

*Primary Examiner*—Katarzyna Wyrozebski
(74) *Attorney, Agent, or Firm*—Marshall, Gerstein & Borun LLP

(57) ABSTRACT

Concentrated suspensions of smectite clays are obtained as either relatively "thin" or highly shear-thinning slurries that are easy to pump, by adding one or more of certain cationic polymers whose weight average molecular weight, Mw, is 50,000 or higher. It was found during the course of the invention that a cationic polymer with an Mw of 10,000 did not work, while the same polymer with a bimodal Mw of 50,000 and 30,000 worked satisfactorily. To achieve the full advantage of the present invention, the cationic polymer preferably has 1 to 10 milliequivalents of cationic charge per gram of the polymer, and more preferably 5 to 10 milliequivalents of cationic charge per gram of the polymer, and most preferably 6 to 8 milliequivalents of cationic charge per gram of the polymer.

22 Claims, No Drawings

NONVISCOUS AQUEOUS DISPERSION COMPOSITIONS OF WATER-SWELLABLE LAYERED SILICATES AND THE METHOD OF PRODUCING THE SAME

SUMMARY OF THE INVENTION

This application is a non-provisional application claiming priority from U.S. Provisional Application Ser. No. 60/425,862, filed Nov. 13, 2002.

The present invention relates to concentrated, aqueous dispersion or aqueous slurry compositions of water-swellable layered silicates such as the smectite clays, which either have unusually low viscosities or have high shear-thinning properties, as well as the ability to coagulate/flocculate suspended materials in water, and a method of producing the compositions. While the weight content of the suspended clay particles in these slurry compositions can be as high as 40-50%, the dispersions remain sufficiently thin or shear-thinning to allow pumping of the slurry. Ordinarily, even at relatively low concentrations (for example 5-10%), smectite clays can bring about significant thickening in aqueous suspensions, often turning the suspensions into gels.

A key object of the present invention is to produce such dispersions of smectite clays, which are amenable to pumping even when the clay content is relatively high, in a manner that renders the dispersion compositions especially suited for coagulating/flocculating suspended matter in wastewater or other water streams. This is achieved by adding one or more cationic polymers with a weight average molecular weight of at least 50,000 Daltons to aqueous clay suspensions, at concentrations sufficient for the cationic polymer(s) to function as a thinning agent for the suspended clay particles.

Thickening or gelation of aqueous suspensions by smectite clays is a manifestation of clay particles forming a network structure due to interparticle associations, that spans through the entire suspension volume, entrapping the suspension medium. A thinning agent acts to minimize such particle-to-particle links by providing for interparticle repulsion upon adsorption on the particle surface. The use of a cationic polymer as a thinning agent leaves the surface of the clay particles cationic such that these cationic particles can draw anionic particles into coagulation/flocculation by bridging two or more of such particles that generally constitute the suspended matter in water streams.

BACKGROUND OF THE INVENTION

Layered silicate materials such as the smectite clays are a class of inorganic particulate materials that occur as stacks of individual, planar silicate layers referred to as platelets in the clay literature. Examples of smectite clays include montmorillonite, bentonite, bidelite, hectorite, saponite, and stevensite. These clays are popular particulate gellants or thickeners for aqueous compositions.

Smectite clays also find use as a flocculation aid in wastewater treatment where the flocculant compositions used are generally solid admixtures of clay and other treatment reagents. These flocculant products, however, are excluded from those wastewater treatment scenarios where the facility is not equipped to handle any solid treatment reagent. Since smectite clay-water slurries turn into gels once the clay content exceeds a level that may be as low as in the range of 5-10% by weight, handling, especially pumping, of clay suspensions with high clay content may prove to be extremely difficult, if not impossible. Nevertheless, in order for it to be viable, any liquid product of clay-based flocculants should have clay content much exceeding the above range. The present invention reveals a method for achieving such desirable liquid products of smectite clay-based flocculants, and the compositions thereof.

The face-surfaces of the platelets of smectite clays bear anionic charges counterbalanced by exchangeable cations that remain electrostatically attracted to the anionic charge of the clay surface. The exchangeable cations are generally either sodium ions or calcium ions. Smectite clay is referred to as sodium or calcium clay, depending on the type of predominant counterions associated with the face-surfaces of the clay platelets. While the anionic charge on the platelet face-surfaces does not vary with pH, the electrical charge on the edge-surfaces of these clays, although anionic under alkaline pH, could be cationic under acidic pH.

Fundamentally, the formation of particulate gels is a manifestation of suspended colloidal particles forming a network structure that entraps and thus immobilizes the suspending medium. Clay-based gels may form when individual platelets or stacks of a few, e.g., 3-15, aggregated platelets (tactoids) engage in interparticle associations with their neighboring platelets. These particle-to-particle links result in a particulate structure pervading through the entire suspension-volume. Such interparticle associations are governed by the interplay between the attractive and repulsive forces that generally act between particles suspended in a liquid.

Clearly, the strength of particulate gels will depend on the number of interparticle associations in a given volume of the gel, implying that the greater the number-concentration of suspended particles, the stronger is the gel. Also, a dominance of the attractive interactions over the repulsive interactions, the likelihood of which increases with decrease in interparticle separation distance, is required for suspended particles to associate with their neighbors. An increase in number-concentration of particles will tend to reduce their separation distances, an effect that could be especially dramatic for planar particles since the separation distance between two adjacent platelets will vary along their lengths when their faces do not align in parallel configuration. Nonetheless, too strong an attraction between adjacent clay platelets may draw them into strong face-to-face association, minimizing the number-concentration of particles.

Considering the above, the key to making clay-based gels is to ensure that there is sufficient interplatelet repulsion for the clay platelets to exfoliate (delaminate) under shear, releasing a large number of platelets as individual platelets or tactoids having fewer stacked platelets, that would then be available to form a particle network. On the other hand, in order to form a voluminous network structure, the net interaction (the sum of attractive and repulsive forces) between the delaminated platelets must be such that they can remain "bound" (attracted) to their neighboring platelets without being drawn into strong face-to-face association. Accordingly, the gel-network may form if the delaminated platelets, while being separated from the surrounding platelets by as thick as possible an intervening layer of the suspending medium, reside in a minimum of free energy of interaction with the neighboring platelets. Albeit physically separated from their neighbors, the individual platelets are no longer free to move independently, being trapped in a free energy minimum, in effect producing a particulate structure, and therefore thickening or gelation. Yet another phenomenon that clay-based gels may form in aqueous compositions, is where clay platelets coagulate due to edge-to-face associations, forming the so-called "card-house" structure described in clay literature.

The sodium smectite clays exfoliate to a much greater extent than their calcium analogs. For this reason, the sodium smectite clays produce a significantly higher level of thickening as compared to the calcium smectite clays. Therefore, one way of having concentrated clay suspensions with high fluidity is to use calcium smectite clays. However, such dispersions, while possibly meeting the requirement of low viscosity, would not present a high number concentration of delaminated platelets, which may be desirable for having good flocculating properties during wastewater treatment.

The ability of clay platelets to bring about coagulation/flocculation of suspended debris particles in wastewater is related to a phenomenon that may be described as heterocoagulation (coagulation between dissimilar materials) between the clay platelets and the debris particles. Such heterocoagulation would occur when the physicochemical conditions of the wastewater are such that the interaction between the debris particles and the clay platelets is attractive, even though the interaction between the debris particles is repulsive, preventing these particles from coagulating. Another way to describe such a heterocoagulation process is to use the analogy of bridging flocculation by polymeric flocculants, as described in colloid literature: like polymeric flocculants, the clay platelets draw the suspended debris particles into flocculation by sticking to and thus bridging two or more debris particles simultaneously.

It may be expected that the aforementioned debris-clay coagulation process will be favored if the number concentration of clay platelets is high (i.e., if the clay platelets are highly delaminated or exfoliated, an effect that also promotes thickening induced by clay platelets) and/or if a strong clay platelet-debris particle attraction is brought into play. Accordingly, conflicting demands are faced in obtaining concentrated, non-viscous clay-suspensions where the clay platelets are sufficiently delaminated in order to have good flocculating power. Nevertheless, even when a large number of clay platelets have been released due to exfoliation, the platelets may be prevented from engaging into any association with the neighboring platelets if the interparticle repulsive forces greatly dominate over the attractive forces. Therefore, the key to attaining concentrated, but non-viscous clay-suspensions, without necessarily sacrificing good exfoliation of clay platelets, is to ensure that strong repulsive forces act between the platelets, superseding any attractive interplatelet forces that tend to bring about associations between the platelets. Most surfaces tend to acquire an anionic charge when wetted with an electrolyte or water. Also, the surface active agents (emulsifiers and dispersing agents) that are more commonly used in industrial applications are anionic, resulting in suspended particles in most wastewater streams that are generally anionic. So in the context of clay-based flocculants, it has been found that a way to increase the clay platelet-debris attraction is to render the surface of the clay platelets cationic through the adsorption of cationic species.

As described in colloid literature, ionic polymers or polyelectrolytes may provide for electrical and steric repulsion forces between suspended particles, if, upon adsorption on the particle surface, i) the adsorbed polymer chains render the particle surface electrically charged, ii) the adsorbed polymer chains occupy more than 50% of the particle surface area, and iii) the polymer segments dangle out off the particle surface into the surrounding dispersion medium, forming loops and tails. Once brought into play, these repulsion forces act to minimize interparticle associations, resulting in thinning of the suspension. The adsorption of cationic polyelectrolytes on the surface of clay platelets could potentially increase the attractive interaction between the clay platelets and the anionic debris particles, which in turn could enhance the flocculating ability of clay.

Although the prior art teaches the use of various types of anionic polymer as thinning agents for smectite clay suspensions, it does not disclose the effects of cationic polymers on the rheological properties (for example, viscosity properties) of concentrated clay suspensions (for example, suspensions having a smectite clay content exceeding 20% by weight). Therefore, it is not clear whether or not the addition of a cationic polymer to a concentrated suspension of smectite clay would produce either a "thin" or a highly shear-thinning suspension that shows a viscosity significantly lower than what it would have been in the absence of the polymer. It is only since the present invention that it has been found that cationic polymers with a weight average molecular weight falling within a certain range, when used even at relatively low concentrations, would render a concentrated suspension of smectite clays non-viscous, while the suspension shows considerable flocculating ability.

Although a targeted application for the product of the present invention is coagulation/flocculation of suspended matter in water streams as, for example, in wastewater treatment, because of the coagulating ability of the product, it may be used even as a drainage aid in the papermaking process, wherein the product helps in bringing about agglomeration of pulp fibers to facilitate the drainage process.

Other potential uses of the product include, but are not limited to, an additive in personal care and cosmetic formulations, as well as a fabric softener. The cationic polymer-modified clays would be substantive to (or adhere onto) the anionic surfaces of the hair or the skin, such that these clays can help deliver some useful hair care or skin care properties when used as an additive in personal care or cosmetic products. For example, the deposition of cationic clay platelets on the anionic surface of the hair shafts is expected to be substantive to hair shafts to enhance hair styling. Accordingly, the use of cationic polymer-modified clays in hair care products should add to the hair styling properties of these products. The prior art discloses the use of smectite clays as a fabric softener. Furthermore, the most commonly used fabric softeners are cationic surfactants. As for the molecular structure, surfactant molecules contain a hydrophilic part and a hydrophobic part, with the two parts of the molecule segregated from one another. The cationic surfactants used as fabric softeners impart softness by adsorbing onto the (negatively charged) fabrics with their hydrophilic part, consisting of the cationic functional group, attached onto the fabric surface, while their hydrophobic part projects outwardly from the surface. Such adsorption of the cationic surfactants minimizes interfacial tension between the fabric surface and the surrounding air mass and minimizes the adhesion of water to the fabric surface. This reduces the shrinkage (reduction of substrate surface area) and resulting hard "feel" that accompanies the removal of water from the substrate. In accordance with the present invention, the cationic modification of the smectite clay surface by the surface treatment of the clay with one or more cationic species, e.g., polymers, that contain one or more hydrophobic groups, render the clay platelets better equipped to serve as a fabric softener.

SUMMARY OF THE INVENTION

The objects of the present invention are as follows:

Produce concentrated suspensions of layered silicate materials, that are amenable to pumping, and show good coagulating/flocculating abilities by surface treating the layered silicate material with cationic polymers.

Provide a method for surface-treating particles of layered silicate materials, that would result in thinning of concentrated suspensions of these particulate materials, while rendering the particles better equipped to function as a coagulant/flocculant Produce a surface-modified clay wherein the clay surface is rendered cationic due to the surface-treatment of the clay with one or more cationic polymer(s), in order that such cationically-modified clays are useful in formulating hair and skin care products as well as a fabric softener Preferably, the weight content of the layered silicate material in the suspension is more than 25%, and the weight ratio of the silicate mineral and the thinning reagent is 4:1 to 10:1. Since one of the targeted application areas, i.e., wastewater treatment, for the product of the present invention, is highly cost-sensitive, it is important that the dosage level of the thinning agent is held relatively low.

DETAILED DESCRIPTION OF THE PREFERRED EMBODIMENTS

The preferred layered silicate materials are phyllosilicates of the 2:1 type with an anionic charge on the face surface, counterbalanced by sodium counterions. More preferably, the layered silicate materials are smectite clays such as montmorillonite, bentonite, bidelite, hectorite, saponite, and stevensite.

According to the present invention, concentrated suspensions of smectite clays are obtained as either relatively "thin" or highly shear-thinning slurries that are easy to pump, by adding one or more of certain cationic polymers whose weight average molecular weight, Mw, is 50,000 or higher. It was found during the course of the invention that a cationic polymer with an Mw of 10,000 did not work, while the same polymer with a bimodal Mw of 50,000 and 30,000 worked satisfactorily. To achieve the full advantage of the present invention, the cationic polymer preferably has 1 to 10 milliequivalents of cationic charge per gram of the polymer, and more preferably 5 to 10 milliequivalents of cationic charge per gram of the polymer, and most preferably 6 to 8 milliequivalents of cationic charge per gram of the polymer.

The word "thin" above refers to such slurry consistency or viscosity as exemplified by the Brookfield RV viscosity (at 10 rpm) of a suspension containing 38% of a sodium smectite clay (based on the total weight of clay and water, the dispersion medium), and under strong agitation by, for example, a shaft-mounted agitator, is less than 6,000 cps, more preferably less than 1,000 cps, and most preferably less than 500 cps. The clay content of the concentrated suspensions of the present invention, expressed as a percentage of the total weight of clay and water (dispersion medium), is in the range of 1-50%, more preferably in the range of 5-45%, and most preferably in the range of 25-45%. The dosage of the cationic polymer based on the dry weight of clay is in the range of 0.1-50%, more preferably in the range of 8-30%, and most preferably in the range of 10-25%.

According to one embodiment of the present invention, the smectite clay is surface-treated with a mixture of low and high molecular weight cationic polymers, wherein the weight average molecular weight of the high molecular weight cationic polymer is at least 50,000. When such mixtures of cationic polymers are used, the weight ratio of the low molecular weight polymer to the high molecular weight polymer is in the range of 10:1 to 1:10, more preferably in the range of 7:1 to 1:7, and most preferably in the range of 1:1 to 1:7.

An important embodiment of the present invention is that the concentrated suspension of cationic polymer-modified layered silicate materials shows coagulating/flocculating abilities either by itself or in conjunction with one or more additional anionic or cationic polymers that are commonly used as a flocculant. By the phrase "coagulating/flocculating ability" is meant the ability to significantly increase the clarity or reduce the turbidity of a water stream that contains suspended matter, by inducing aggregation of most or all of the suspended matter, forming aggregated particles or flocs, for easy separation from the water.

The most preferred cationic polymers that can be used in producing thin, concentrated suspensions of layered silicate materials include but not limited to poly (diallyldimethylammonium chloride) referred to herein as poly(DADMAC), polyquaternary amine polymers prepared from epichlorohydrin and dimethylamine referred to herein as EPI/DMA, and their copolymers with non-ionic, water-soluble polymers. Cationic polymers having weight average molecular weights of 50,000 or higher, derived from natural polymers such as tannin, starch, proteins, guar gum, lignin, lignosulfonate, and humate can also be used. Polyalkyl amines or polyaryl amines having a weight average molecular weight of at least 50,000 can be used as well. For use in personal care and cosmetic product formulations, any cationic polymer with a weight average molecular weight of at least 50,000, including various cationic copolymers that are used in hair and/or skin care products may be useful. Film forming cationic polymers (for example, chitosan polymers or copolymers; cationic polymers or copolymers containing polyvinyl pyrrolidone; polyacrylate; and polyalkylmethacrylate); cationic polymers or copolymers containing hydroxyl, carboxyl, carbonyl, phenolic, and/or ether groups; as well as cationic polymers or copolymers that contain a strong hydrophobic moiety such as an alkyl chain of $C_8$ or higher, and one or more aromatic groups may be used when the product of the present invention is used in personal care and cosmetic formulations.

In accordance with another embodiment of the present invention, the dispersions of cationic polymer-modified clay further contain one or more coagulation/flocculation aids such as a salt of monovalent, and preferably multivalent, cations such as aluminum, iron, and calcium.

For wastewater treatment, the dosage of the product of the present invention, based on the sum of the weights of the dry clay and the dry cationic polymer, could be in the range of 1 ppm-10,000 ppm, more preferably in the range of 10 ppm-1000 ppm, and most preferably in the range of 10 ppm-500 ppm. For the fabric softening application, the product dosage, based on the sum of the weights of the dry clay and the dry cationic polymer, could be in the range of 0.005%-30% of the total weight of the fabric softener formulation, more preferably in the range of 1%-20%, and most preferably in the range of 1%-10% of the formulation. A detergent product that may contain the product of the present invention as a fabric softener component of the formulation may be eventually used in a diluted form, for example, as encountered in a wash cycle of a commercial washer. For hair and skin product formulations, the dosage of the product of the present invention, based on the sum of the weights of the dry clay and the dry cationic polymer, could be in the range of 0.005%-10% of the hair or skin care product formulation, more preferably 0.005%-5% of the formulation, and most preferably 1%-5% of the formulation. Since hair and/or skin care products generally contain a vehicle or a solvent, the solvent composition should contain at least 20% by weight of water, in order to get the full benefit of the present invention.

In the present invention, the thin, concentrated suspensions of layered silicate materials are produced by adding a single layered silicate material, or a mixture of layered silicate materials to an aqueous solution of one or more of the aforementioned types of cationic polymers, and then shearing the resulting suspension using a shearing device such as a shaft-mounted shearing agitator, a rotor-stator mixer, a homogenizer, a media mill, or a colloid mill for a period of time to at least partially exfoliate the layered silicate material(s).

In order to illustrate the present invention clearly, the following examples and data are presented. However, they should not be construed as limiting the scope of the invention to their details.

EXAMPLE 1

This example shows the thinning ability of poly(DAD-MAC) (ZETAG 7131, weight average molecular weight, Mw=100,000, obtained from Ciba Specialty Chemicals) in concentrated suspensions of smectite clay. The procedure followed in carrying out the slurry-viscosity tests for evaluating the cationic polymer is as follows: 76 grams of a sodium smectite clay (ACCOFLOC obtained from CETCO/AMCOL International and POLARGEL NF obtained from ACC/Amcol International) was slowly added to an aqueous solution of the cationic polymer, and sheared in a multi-speed Waring blender, while the blender was operated at speed 1. Immediately after the entire amount of clay was added, the resulting slurry was homogenized at speed 7 (22,000 rpm) of the blender for 5 minutes. The suspension thus produced was transferred to a plastic container and the viscosity was measured in a Brookfield RV viscometer. The slurry-viscosity was measured after 20-25 minutes from the time of completion of mixing, at shear rates corresponding to 10, 20, 50, and 100 rpm of spindle speed in a Brookfield RV viscometer. After completion of viscosity measurements, the lid of the slurry container was replaced and the suspension was shaken vigorously by hand for a brief period of time, after which the slurry viscosity was measured again at 10 rpm. The results of the slurry viscosity tests are shown in Table I.

TABLE I

| Test # | Clay | Cationic Polymer, g | Tap Water, g | Time Since Completion of Mixing, minutes | Rpm | Brookfield Viscosity, cps | Viscosity after Manual Shaking, cps |
|---|---|---|---|---|---|---|---|
| 1 | ACCOFLOC | 27.14 ZETAG 7131 (35% solids) | 106.46 | 20 | 10 20 50 100 | 350 250 178 159 | 75 |
| 2 | ACCOFLOC | 32.57 ZETAG 7131 | 102.93 | 20 | 10 20 50 100 | 120 115 108 110 | 60 |
| 3 | POLARGEL NF | 21.71 ZETAG 7131 | 109.99 | 20 | 10 20 50 100 | 12,000 6,750 3,000 1,775 | 2,000 |
| 4 | POLARGEL NF | 27.14 ZETAG 7131 | 106.46 | 20 | 10 20 50 100 | 4,200 2,350 1,080 660 | 475 |
| 5 | POLARGEL NF | 32.73 ZETAG 7131 | 102.83 | 20 | 10 20 50 100 | 4,400 2,550 1,300 800 | 475 |

It should be noted that the slurries from tests 3 through 5 thickened up to the consistency of a gel after about 16 days of standing. However, upon shaking the slurry containers vigorously by hand for a brief period of time, the suspensions from tests 4 and 5 showed high shear thinning, with 890 cps and 750 cps, respectively, being their Brookfield viscosities at 10 rpm.

EXAMPLE 2

This example shows the efficacy of EPI/DMA (SUPERFLOC C-573 Flocculant, bimodal weight average molecular weight, Mw=50,000 and 30,000, from Cytec Industries, and ZETAG 7191, weight average molecular weight, Mw=50,000, from Ciba Specialty Chemicals) as a thinning agent in concentrated sodium smectite clay suspensions, based on slurry-viscosity tests. The procedure followed in carrying out the slurry-viscosity tests is the same as that described in EXAMPLE 1. The results of the slurry viscosity tests are shown in Table II.

TABLE II

| Test # | Clay | Cationic Polymer, g | Tap Water, g | Time Since Completion of Mixing, minutes | Rpm | Brookfield Viscosity, cps | Viscosity after Shaking, cps |
|---|---|---|---|---|---|---|---|
| 1 | ACCOFLOC | 19 C-573 (50% solids) | 114.6 | 23 | 10 | 3,000 | Viscous |
|   |   |   |   |   | 20 | 1,375 |   |
|   |   |   |   |   | 50 | 900 |   |
|   |   |   |   |   | 100 | 580 |   |
| 2 | ACCOFLOC | 22.8 C-573 | 112.7 | 20 | 10 | 700 | 40 |
|   |   |   |   |   | 20 | 500 |   |
|   |   |   |   |   | 50 | 240 |   |
|   |   |   |   |   | 100 | 190 |   |
| 3 | ACCOFLOC | 26.6 C-573 | 110.8 | 20 | 10 | 260 | 12 |
|   |   |   |   |   | 20 | 165 |   |
|   |   |   |   |   | 50 | 95 |   |
|   |   |   |   |   | 100 | 69 |   |
| 4 | ACCOFLOC | 22.8 ZETAG 7191 | 112.7 | 30 | 10 | 3,700 | 40 after about 6 hours from the time of mixing |
|   |   |   |   |   | 20 | 1,300 |   |
|   |   |   |   |   | 50 | 480 |   |
|   |   |   |   |   | 100 | 390 |   |

EXAMPLE 3

This example shows that cationic reagents having a relatively low weight average molecular weight would not work well as thinning agents for concentrated suspensions of sodium smectite clay. The cationic reagents evaluated include SUPERFLOC C-572 Flocculant (Mw=10,000, from Cytec Industries), and AGEFLEX (monomer for the DADMAC polymer from Ciba Specialty Chemicals). Slurry viscosity tests were carried out the same as in the previous examples.

TABLE III

| Test # | Clay | Cationic Polymer, g | Tap Water, g | Time Since Completion of Mixing, minutes | Rpm | Brookfield Viscosity, cps | Viscosity after Shaking, cps |
|---|---|---|---|---|---|---|---|
| 1 | ACCOFLOC | 22.8 C-572 (50% solids) | 112.7 | 30 | 10 | 10,800 |   |
|   |   |   |   |   | 20 | 5,350 |   |
|   |   |   |   |   | 50 | 2,760 |   |
|   |   |   |   |   | 100 | 1,320 |   |
| 2 | ACCOFLOC | 30.4 C-572 | 108.9 | 35 | 10 | 4,300 | 5,250 |
|   |   |   |   |   | 20 | 2,875 |   |
|   |   |   |   |   | 50 | 1,360 |   |
|   |   |   |   |   | 100 | 750 |   |
| 3 | ACCOFLOC | 38 C-572 | 105.1 | 20 | 10 | 4,100 | 3,300 |
|   |   |   |   |   | 20 | 2,300 |   |
|   |   |   |   |   | 50 | 980 |   |
|   |   |   |   |   | 100 | 530 |   |
| 4 | ACCOFLOC | 27.14 Ageflex (70% solids) | 115.96 | 20 | 10 | 4,200 | 2,700 |
|   |   |   |   |   | 20 | 2,400 |   |
|   |   |   |   |   | 50 | 1,860 |   |
|   |   |   |   |   | 100 | 1020 |   |

EXAMPLE 4

This example shows the slurry thinning ability of mixtures of cationic polymers, ZETAG 7131, with Mw=100,000, and ZETAG 7122, with Mw=425,000, in a concentrated suspension of sodium bentonite clay. Similar slurry-viscosity tests as in the previous examples were carried out.

TABLE IV

| Test # | Clay | Cationic Polymer, g | Tap Water, g | Time Since Completion of Mixing, minutes | Rpm | Brookfield Viscosity, cps | Viscosity after Shaking, cps |
|---|---|---|---|---|---|---|---|
| 1 | ACCOFLOC | 32.57 ZETAG 7131, 15% polymer on clay | 102.93 | 20 | 10 20 50 100 | 120 115 108 110 | 60 |
| 2 | ACCOFLOC | 57 Zetag 7122, 15% polymer on clay | 78.5 | 20 | 10 20 50 100 | 19,750 14,375 9,460 6,940 | 17,500 |
| 3 | ACCOFLOC | 16.29 ZETAG 7131, 7.5% polymer on clay | 113.41 | 20 | 10 20 50 100 | Highly viscous | |
| 4 | ACCOFLOC | 28.5 ZETAG 7122, 7.5% polymer on clay | 101.2 | 20 | 10 20 50 100 | Highly viscous | |
| 5 | ACCOFLOC | 28.5 ZETAG 7122 + 16.29 ZETAG 7131, 15% polymer on clay | 90.61 | 20 | 10 20 50 100 | 1,500 1,300 1,100 940 | 700 |
| 6 | ACCOFLOC | 76 ZETAG 7122 + 6.51 ZETAG 7131, 23% polymer on clay | 58.97 | 20 | 10 20 50 100 | 4,250 3,700 3,120 2,760 | |

EXAMPLE 5

This example shows the coagulating/flocculating ability of a concentrated suspension of sodium smectite clay, wherein poly(DADMAC) is used as the thinning agent for the slurry. The clay suspension is identical in composition to the clay suspension in Test 1 of EXAMPLE 1. Flocculation tests were carried out by adding a given weight of the clay suspension to 100 grams of an industrial wastewater sample having poor clarity or high turbidity. In some cases, a measured amount of a 15% alum solution was added to the wastewater sample along with the clay suspension. After mixing (using a magnetic stirrer) the clay suspension and/or the alum solution with the wastewater for 1 minute, an aliquot of a dilute solution (0.1%-1% by weight) of an anionic flocculant (sodium polyacrylate) marketed under the trade-name of F730A by CETCO was added to the wastewater, and mixing was continued for an additional 1.25 minutes during which time the suspended materials contained in the wastewater separated out as large flocs. The treated wastewater thus obtained was filtered, and the filtrate was taken for % Transmittance (% T) measurement (at 620 nm wavelength) in a Hach Spectrophotometer calibrated with deionized water for 100% T. A high value of % T indicates a high level of clarification or a low level of turbidity.

TABLE V

| Test # | Wastewater sample ID | Clay Suspension, g | 15% Alum solution, g | Anionic polymer, g | pH | % T | Comments |
|---|---|---|---|---|---|---|---|
| 1 | Thomas Betts | 0 | 0.3 | 6, 0.1% solution of F730A | | | No clarification |
| 2 | Same as above | 0.25 | 0.3 | 6, 0.1% solution of F730A | 7.39 | 94 | |
| 3 | Same as above | 0.3 | 0.35 | 6, 0.1% solution of F730A | 7.18 | 95 | |
| 4 | Same as above | 0.35 | 0.3 | 6, 0.1% solution of F730A | 7.86 | 97 | |

TABLE V-continued

| Test # | Wastewater sample ID | Clay Suspension, g | 15% Alum solution, g | Anionic polymer, g | pH | % T | Comments |
|---|---|---|---|---|---|---|---|
| 5 | Muellor Vibratory | 0.3 | 0.3 | 0.28, 1% solution of F730A | 8.99 | 97 | |
| 6 | Muellor Vibratory | 0.3 | 0 | 0.3 1% solution of F730A | 9.09 | 98 | |

EXAMPLE 6

This example shows the coagulating/flocculating ability of sodium bentonite dispersions containing mixtures of cationic polymers, ZETAG 7131, with Mw=100,000, and ZETAG 7122, with Mw=425,000. The compositions of the dispersions tested are given below.

| Slurry # 1 | |
|---|---|
| ACCOFLOC clay = | 100 g |
| ZETAG 7131 = | 22.86 g |
| ZETAG 7122 = | 22.5 g |
| Tap water = | 91.14 g |
| Slurry # 2 | |
| ACCOFLOC clay = | 100 g |
| ZETAG 7131 = | 8.57 g |
| ZETAG 7122 = | 100 g |
| Tap water = | 47 g |

The dispersions were tested for clarifying ability in a sample of a laundry wastewater. The results of these flocculation tests are shown in Table VI.

TABLE VI

| Test # | Slurry # | Clay Suspension, ppm | Anionic Polymer, ppm | % T |
|---|---|---|---|---|
| 1 | 1 | 780 | 10 | 97 |
| 2 | 2 | 300 | Approximately 10-30 | 94.5 |

What is claimed is:

1. A method of treating hair for improved styling comprising contacting said hair with an aqueous suspension of a water-soluble cationic polymer having a weight average molecular weight of at least 50,000 and a sodium smectite clay sheared sufficiently to at least partially exfoliate the clay, wherein the amount of the sodium smectite clay exceeds 20 weight percent based on the total weight of the suspension, and wherein the aqueous suspension has a Brookfield RV viscosity, at 10 rpm, less than 6,000 cps, when measured at 38% sodium smectite clay, based the total weight of clay and water.

2. The method of claim 1 wherein the combined amount of the sodium smectite clay and cationic polymer contacting the hair is in the range of 0.005% to 10%, based on the weight of the hair contacted therewith.

3. The method of claim 2 wherein the combined amount of the sodium smectite clay and cationic polymer contacting the hair is in the range of 0.0005% to 5%, based on the weight of the hair contacted therewith.

4. The method of claim 3 wherein the combined amount of the sodium smectite clay and cationic polymer contacting the hair is in the range of 1% to 5%, based on the weight of the hair contacted therewith.

5. The method of claim 1 wherein the sodium smectite clay and cationic polymer are dispersed in a mixture of water and an organic solvent, wherein the water is included in an amount of at least 20% based on the total weight of water and organic solvent.

6. The method of claim 1 wherein the amount of the sodium smectite clay is from greater than 20 weight percent to 50 weight percent based on the total weight of the suspension.

7. The method of claim 6 wherein the amount of the sodium smectite clay is from 25 weight percent to 50 weight percent based on the total weight of the suspension.

8. The method of claim 7 wherein the amount of the sodium smectite clay is from 25 weight percent to 45 weight percent based on the total weight of the suspension.

9. The method of claim 1 wherein the weight ratio of sodium smectite clay to the cationic polymer is 2:1 to 1000:1.

10. The method of claim 1 wherein the amount of cationic polymer in the suspension is in the range of 0.1% to 50% based on the dry weight of the sodium smectite clay.

11. The method of claim 10 wherein the amount of cationic polymer in the suspension is in the range of 8% to 30% based on the dry weight of the sodium smectite clay.

12. The method of claim 11 wherein the amount of cationic polymer in the suspension is in the range of 10% to 25% based on the dry weight of the sodium smectite clay.

13. The method of claim 1 wherein the cationic polymer has 1 to 10 milliequivalents of cationic charge per gram of the polymer.

14. The method of claim 13 wherein the cationic polymer has 5 to 10 milliequivalents of cationic charge per gram of the polymer.

15. The method of claim 14 wherein the cationic polymer has 6 to 8 milliequivalents of cationic charge per gram of the polymer.

16. The method of claim 1 wherein the suspension contains a mixture of a lower molecular weight cationic polymer and a higher molecular weight cationic polymer, at least one of which has a weight average molecular weight at least 50,000.

17. The method of claim 16, wherein the weight ratio of the lower molecular weight cationic polymer to the higher molecular weight cationic polymer is in the range of 10:1 to 1:10.

18. The method of claim 17, wherein the weight ratio of the lower molecular weight cationic polymer to the higher molecular weight cationic polymer is in the range of 7:1 to 1:7.

19. The method of claim 18, wherein the weight ratio of the lower molecular weight cationic polymer to the higher molecular weight cationic polymer is in the range of 1:1 to 1:7.

20. The method of claim 1, wherein the water-soluble cationic polymer has a weight average molecular weight of 100,000 to 425,000.

21. The method of claim 1, wherein the cationic polymer is selected from the group consisting of polydiallyldimethylammonium chloride; polyquaternary amine polymers prepared from epichlorohydrin and dimethylamine, and their copolymers with non-ionic water-soluble polymers.

22. The method of claim 1, wherein the cationic polymer is derived from natural polymers selected from the group consisting of tannin; starch; a protein; guar gum; lignin; lignosulfonate; humate; polyalkyl amine; and polyaryl amine.

* * * * *

UNITED STATES PATENT AND TRADEMARK OFFICE
CERTIFICATE OF CORRECTION

PATENT NO.        : 7,378,466 B2                                    Page 1 of 1
APPLICATION NO. : 10/706752
DATED             : May 27, 2008
INVENTOR(S)       : Ashoke K. SenGupta et al.

It is certified that error appears in the above-identified patent and that said Letters Patent is hereby corrected as shown below:

<u>Title Page, Item (75) Inventors:</u>

Fourth named Inventor, "Iiona" should be -- Ilona --.

<u>Title Page, Item (73) Assignee:</u>

"Corp." should be -- Corporation --.

<u>In the Claims:</u>

At Column 13, line 60, "based the" should be -- based on the --.

Signed and Sealed this

Twenty-fourth Day of March, 2009

JOHN DOLL
*Acting Director of the United States Patent and Trademark Office*